US010898400B2

(12) United States Patent
Kostic et al.

(10) Patent No.: US 10,898,400 B2
(45) Date of Patent: Jan. 26, 2021

(54) PERSON SUPPORT APPARATUSES WITH LOAD CELLS

(71) Applicant: Stryker Corporation, Kalamazoo, MI (US)

(72) Inventors: Marko N. Kostic, Portage, MI (US); Sujay Sukumaran, Portage, MI (US); Jonathan Mark Greenbank, Plainwell, MI (US)

(73) Assignee: Stryker Corporation, Kalamazoo, MI (US)

( * ) Notice: Subject to any disclaimer, the term of this patent is extended or adjusted under 35 U.S.C. 154(b) by 373 days.

(21) Appl. No.: 15/826,779

(22) Filed: Nov. 30, 2017

(65) Prior Publication Data

US 2018/0153753 A1   Jun. 7, 2018

Related U.S. Application Data

(60) Provisional application No. 62/428,834, filed on Dec. 1, 2016.

(51) Int. Cl.
*A61G 7/05* (2006.01)
*A61G 7/012* (2006.01)
(Continued)

(52) U.S. Cl.
CPC .............. *A61G 7/0527* (2016.11); *A61B 5/11* (2013.01); *A61G 7/012* (2013.01); *A61G 7/015* (2013.01); *A61G 7/018* (2013.01); *A61G 2203/44* (2013.01)

(58) Field of Classification Search
CPC ...... A61G 7/0527; A61G 7/012; A61G 7/015; A61G 7/018; A61G 2203/44; A61B 5/1036; A61B 5/1115; A61B 5/11; A61B 5/1113; H03M 1/12; H03M 1/1245; H03M 1/125; H03M 1/1255; H03M 1/126;
(Continued)

(56) References Cited

U.S. PATENT DOCUMENTS 4,131,802 A  *  12/1978  Braden ................ A61B 6/0442
                                                    250/363.02
4,483,404 A      11/1984  Weihs
(Continued)

FOREIGN PATENT DOCUMENTS

EP            0744598 A1    11/1996

*Primary Examiner* — Nicholas F Polito
*Assistant Examiner* — Morgan J McClure
(74) *Attorney, Agent, or Firm* — Warner Norcross + Judd LLP

(57) ABSTRACT

A person support apparatus, such as a bed, cot, stretcher, chair, or the like, includes a frame, a support surface supported by the frame, a plurality of load cells that detect weight supported on the support surface, at least one A/D converter, and a controller. The load cells output analog signals that are converted to digital by the A/D converters. The controller switches a sampling rate of the A/D converters between at least first and second rates. The outputs from the load cells are forwarded to a plurality of signal acquisition nodes that include the A/D converters. The nodes are positioned at locations that minimize the length of travel of the analog signals, thereby reducing noise interference. Shivering, occupant absence/presence, vital signs, occupant movement, and/or other parameters are detected by the load cells.

19 Claims, 8 Drawing Sheets

(51) Int. Cl.
*A61G 7/015* (2006.01)
*A61G 7/018* (2006.01)
*A61B 5/11* (2006.01)

(58) Field of Classification Search
CPC .. H03M 1/1265; H03M 1/127; H03M 1/1275; H03M 1/1285
See application file for complete search history.

(56) References Cited

U.S. PATENT DOCUMENTS

| | | |
|---|---|---|
| 4,540,057 A | 9/1985 | Freeman |
| 4,549,622 A | 10/1985 | Leiman |
| 4,581,948 A | 4/1986 | Reichow |
| 4,593,778 A | 6/1986 | Konishi et al. |
| 4,785,797 A * | 11/1988 | Cuervo ............... A47C 9/022 5/109 |
| 4,815,547 A * | 3/1989 | Dillon ............... G01G 3/1406 177/211 |
| 4,932,253 A | 6/1990 | McCoy |
| 4,974,692 A | 12/1990 | Carruth et al. |
| 5,098,200 A * | 3/1992 | O'Brien ............... G05D 23/24 374/163 |
| 5,276,432 A | 1/1994 | Travis |
| 6,469,263 B1 | 10/2002 | Johnson |
| 6,822,571 B2 | 11/2004 | Conway |
| 6,924,441 B1 | 8/2005 | Mobley et al. |
| 6,987,226 B2 | 1/2006 | Sakai et al. |
| 7,437,787 B2 * | 10/2008 | Bhai ............... A61B 5/1115 177/144 |
| 7,642,943 B1 * | 1/2010 | Cetin ............... H03M 1/007 323/272 |
| 7,699,784 B2 | 4/2010 | Wan Fong et al. |
| 7,971,300 B2 * | 7/2011 | Wilker, Jr. ......... A61G 7/05776 5/655.3 |
| 8,381,336 B2 | 2/2013 | Kazuno et al. |
| 8,599,025 B2 | 12/2013 | Cipriano |
| 8,711,026 B1 * | 4/2014 | Kappes ............... H03M 1/12 341/155 |
| 8,836,498 B2 * | 9/2014 | Tatinclaux ........... A61B 5/6892 340/501 |
| 8,978,181 B2 | 3/2015 | Menke et al. |
| 9,320,444 B2 | 4/2016 | Hayes et al. |
| 9,552,714 B2 | 1/2017 | Ribble et al. |
| 2007/0163045 A1 * | 7/2007 | Becker ............... A61B 5/6887 5/616 |
| 2009/0195432 A1 * | 8/2009 | Bailey ............... H03M 1/146 341/156 |
| 2013/0247300 A1 * | 9/2013 | Menke ............... A61G 13/0018 5/611 |
| 2013/0283530 A1 * | 10/2013 | Main ............... A47C 31/12 5/600 |
| 2014/0069729 A1 | 3/2014 | Shih |
| 2015/0335507 A1 * | 11/2015 | Emmons ............... G16H 20/00 5/615 |
| 2016/0106345 A1 | 4/2016 | Kostic et al. |
| 2016/0156365 A1 * | 6/2016 | Scherr ............... H03M 1/144 341/156 |
| 2016/0310045 A1 | 10/2016 | Hoffman et al. |
| 2017/0003159 A1 | 1/2017 | Kostic et al. |
| 2017/0128296 A1 | 5/2017 | Kostic et al. |
| 2017/0243459 A9 | 8/2017 | Sidhu et al. |
| 2019/0181860 A1 * | 6/2019 | Cholasta ............ H03K 17/9622 |

* cited by examiner

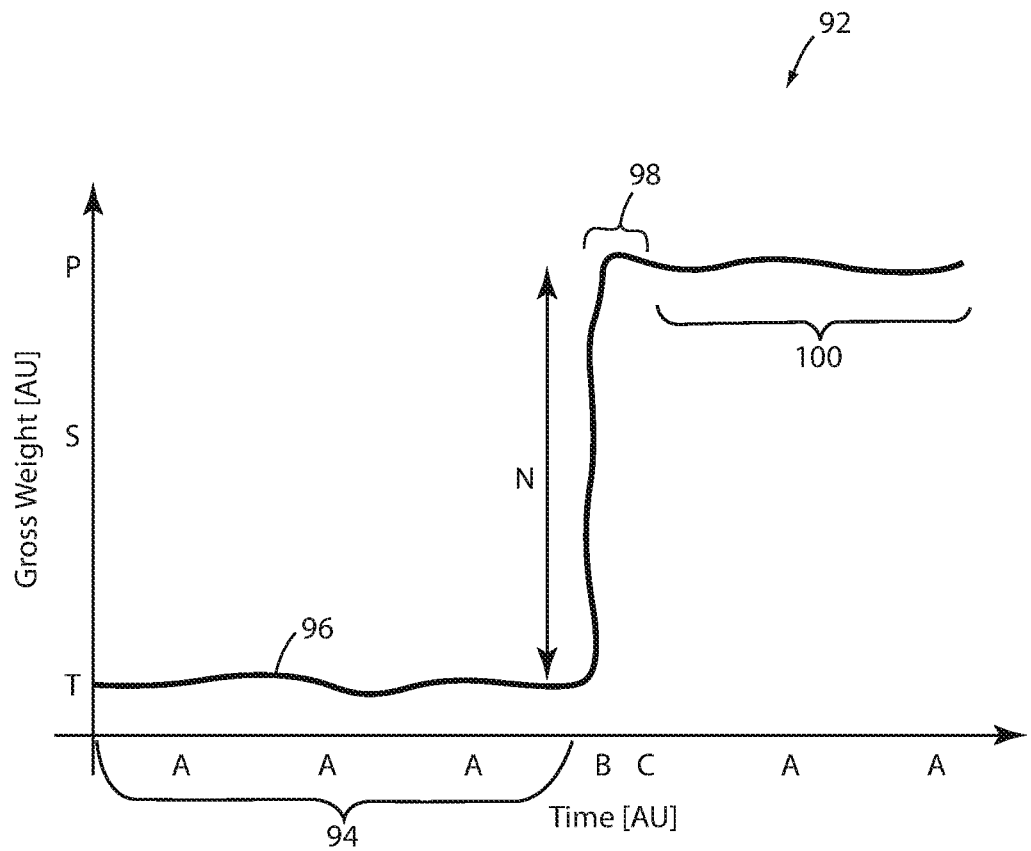

A - Periodic low-sampling data rate acquisition for weight accuracy (algorithms may use several last accurate values of weight, e.g., 3)
B - Patient detection event using high-sampling data rate for transient event detection
C - Low-sampling data rate acquisition for weight accuracy after patient is detected
N - Patient net weight
P - Patient weight level
S - patient event trigger level
T - Tare weight level

FIG. 8

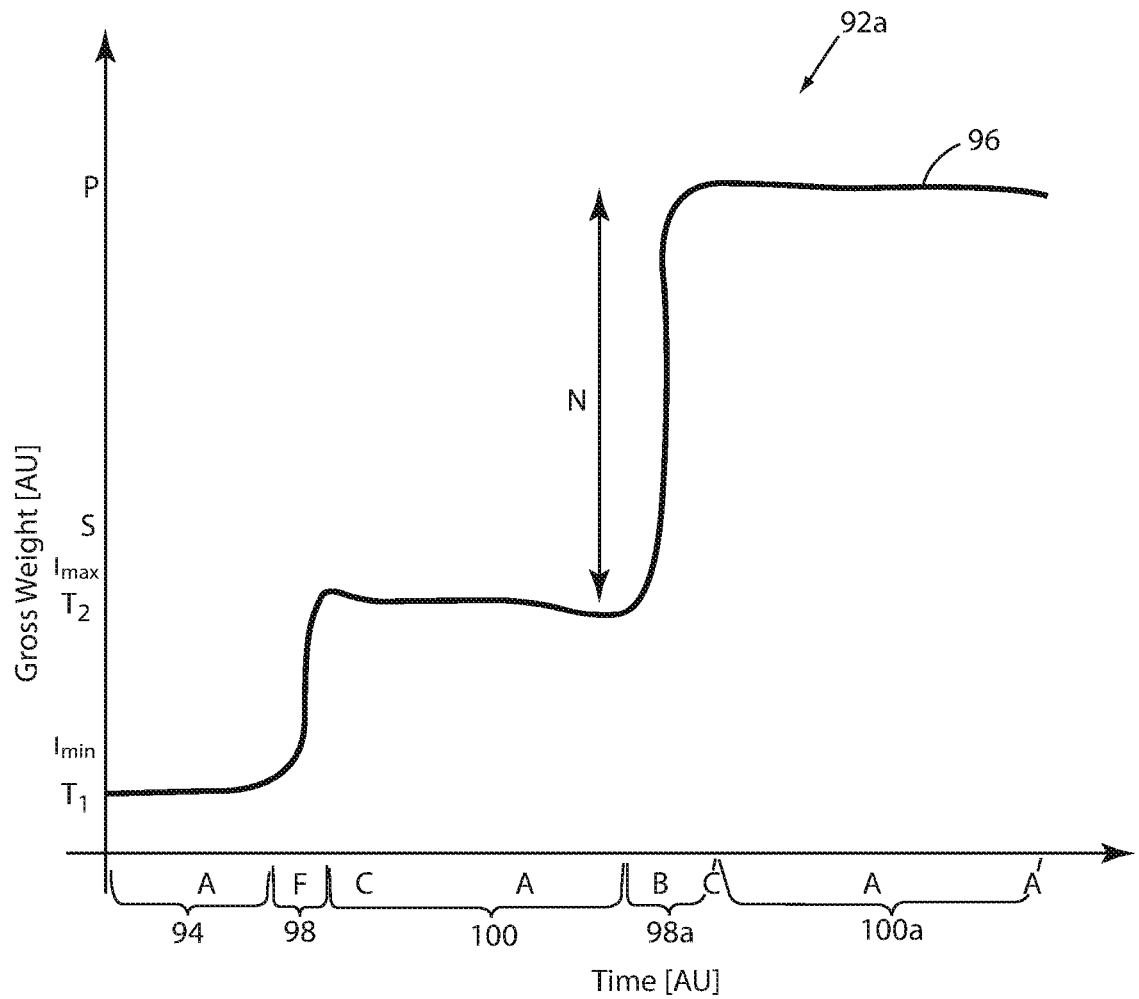

A - Periodic low-sampling data rate acquisition for weight accuracy (algorithms may use several last accurate values of weight, e.g., 3)
B - Patient detection event using high-sampling data rate for transient event detection
C - Low-sampling data rate acquisition for weight accuracy after patient/item is detected
I - Item event trigger level range (minimum to maximum item weight)
N - Patient net weight
P - Patient weight level
S - patient event trigger level
T - Tare weight level ($T_1$ original tare; $T_2$ new tare with item added)

FIG. 9 ively be # PERSON SUPPORT APPARATUSES WITH LOAD CELLS

CROSS-REFERENCE TO RELATED APPLICATIONS

This application claims priority to U.S. provisional patent application Ser. No. 62/428,834 filed Dec. 1, 2016, by inventors Marko Kostic et al. and entitled PERSON SUPPORT APPARATUSES WITH LOAD CELLS, the complete disclosure of which is incorporated herein by reference.

BACKGROUND

The present disclosure relates to person support apparatuses, such as beds, cots, stretchers, operating tables, recliners, or the like. More specifically, the present disclosure relates to person support apparatuses that include load cells.

Existing hospital beds and/or stretchers often include a load cell system that is used to detect the weight of an occupant of the bed or stretcher, and/or that is used as an exit detection system. When functioning as a scale system, the outputs of the load cells are read and a weight of the occupant is detected. When functioning as an exit detection system, the outputs of the load cells are read and used to detect when a patient has exited the bed or stretcher, or when a patient may be about to exit the bed or stretcher.

SUMMARY

According to various embodiments, the present disclosure provides a person support apparatus having an improved load cell system that is configured to provide more accurate results. In some embodiments, the person support apparatus includes load cells whose outputs are better shielded from Electromagnetic Interference (EMI). The person support apparatus may also or alternatively include analog-to-digital converters that operate at multiple sampling rates whereby the sampling rates are automatically controlled based on one or more conditions. In some embodiments, the load cells are used to monitor and log the times at which a person has been on the person support apparatus and the times at which the person has been out of the person support apparatus. Automatic taring of the scale system may also or alternatively be included.

According to one embodiment, a person support apparatus is provided that includes a frame, a plurality of load cells, a support surface, an analog-to-digital converter, and a controller. The load cells are supported by the frame and adapted to output analog signals indicative of loads detected by the load cells. The support surface supports thereon an occupant of the person support apparatus and is configured such that a weight of the occupant is detectable by the load cells when the occupant is positioned on the support surface. The analog-to-digital converter converts the analog signals from at least one of the load cells into digital signals at a first rate and at a second rate. The controller switches the analog-to-digital converter between the first rate and the second rate.

According to another embodiment, a person support apparatus is provided that includes a frame, a plurality of load cells, a support surface, a first signal acquisition node, a second signal acquisition node, and a controller. The load cells are supported by the frame and adapted to output analog signals indicative of loads detected by the load cells. The support surface is adapted to support thereon an occupant of the person support apparatus. The support surface is supported by the load cells such that a weight of the occupant is detectable by the load cells when the occupant is positioned on the support surface. The first signal acquisition node comprises a first analog-to-digital converter adapted to convert analog signals from a first one of the load cells into digital signals. The second signal acquisition node is spaced away from the first signal acquisition node and comprises a second analog-to-digital converter. The second analog-to-digital converter converts analog signals from a second one of the load cells into digital signals. The controller is spaced from the first and second signal acquisition nodes and coupled thereto by wires. The controller determines a weight supported on the support surface based upon the digital signals from the first and second signal acquisition nodes.

According to another embodiment, a person support apparatus is provided that includes a frame, load cells, a support surface, an analog-to-digital converter, and a controller. The load cells are supported by the frame and adapted to output analog signals indicative of loads detected by the load cells. The support surface is adapted to support thereon an occupant of the person support apparatus. The support surface is supported by the load cells such that weight supported on the support surface is detectable by the load cells. The analog-to-digital converter converts analog signals from at least one of the load cells into digital signals at a first rate and at a second rate. The controller detects when weight is added and removed from the support surface and switches between the first and second rates based on detecting added weight and removed weight.

According to still another embodiment, a person support apparatus is provided that includes a frame, a plurality of load cells, a support surface, and a controller. The load cells are supported by the frame and are each adapted to output analog signals indicative of loads detected by the load cells. The support surface is adapted to support thereon an occupant of the person support apparatus. The support surface is supported by the load cells such that weight supported on the support surface is detectable by the load cells. The controller uses outputs from the load cells to detect and record an entry time when the occupant enters the person support apparatus and to detect and record an exit time when the occupant exits the person support apparatus.

According to other aspects, the controller switches between the first and second rates of the analog-to-digital converters based upon the digital signals output from the analog-to-digital converters.

In some embodiments, the first rate is more than one hundred times as fast as the second rate.

The controller is adapted to switch from a slow rate to a fast rate, in some embodiments, whenever a change above a threshold amount occurs in the digital signals from an analog-to-digital converter. Alternatively, or additionally, the controller is adapted to switch to the slow rate when changes above the threshold amount are not detected for a threshold time in the digital signals.

The controller uses the digital signals from the at least one of the load cells to determine a weight of the occupant in some embodiments. When doing so, the controller determines the weight of the occupant when the analog-to-digital converter is operating at the slow rate.

The controller is programmed, in some embodiments, to automatically determine a tare weight before the occupant enters the support surface.

In some embodiments, the controller uses the digital signals from the load cells to determine when the occupant enters the person support apparatus and when the occupant exits the person support apparatus. The controller also records an entry time when the occupant enters the person support apparatus and an exit time when the occupant exits the person support apparatus. The controller is adapted to display the entry time and exit time on a display of the person support apparatus. In some embodiments, the person support also includes a transceiver adapted to communicate with an off-board device, and the controller transmits the entry time and exit time to the off-board device.

In some embodiments, the first signal acquisition node sends the digital signals from the first analog-to-digital converter to the second signal acquisition node, and the second signal acquisition node sends the digital signals from both the first and second analog-to-digital converters to the controller. The first signal acquisition node and the first one of the load cells are both positioned adjacent a head end of the person support apparatus, in at least one embodiment. In such embodiments, the second signal acquisition node and the second one of the load cells are both positioned adjacent a foot end of the person support apparatus.

In some aspects of the disclosure, the first and second signal acquisition nodes include first and second filters adapted to filter out frequencies above a threshold in the analog signals from the load cells.

The first signal acquisition node may include first processing circuitry adapted to analyze the digital signals from the first analog-to-digital converter to determine whether to operate the first analog-to-digital converter at the first rate or the second rate. In such embodiments, the second signal acquisition node includes second processing circuitry adapted to analyze the digital signals from the second analog-to-digital converter to determine whether to operate the second analog-to-digital converter at the first rate or the second rate.

According to other aspects, the controller is configured to automatically distinguish between weight changes resulting from the occupant entering or exiting the person support apparatus and weight changes resulting from objects added to or removed from the person support apparatus.

The load cells may be part of an exit detection system having an armed state in which the controller issues an alert when the occupant exits the person support apparatus and a disarmed state in which the controller does not issue an alert when the occupant exits the person support apparatus. In such embodiments, the controller detects when weight is added and removed from the support surface when the exit detection system is in both the armed state and the disarmed state. The controller may be further adapted to automatically change the exit detection system to the armed state after the occupant enters the person support apparatus.

In some embodiments, the person support apparatus includes at least four load cells.

In any of the person support apparatuses described herein, the person support apparatus may be one of a bed, a recliner, a cot, and a stretcher.

Before the various embodiments disclosed herein are explained in detail, it is to be understood that the claims are not to be limited to the details of operation or to the details of construction and the arrangement of the components set forth in the following description or illustrated in the drawings. The embodiments described herein are capable of being practiced or being carried out in alternative ways not expressly disclosed herein. Also, it is to be understood that the phraseology and terminology used herein are for the purpose of description and should not be regarded as limiting. The use of "including" and "comprising" and variations thereof is meant to encompass the items listed thereafter and equivalents thereof as well as additional items and equivalents thereof. Further, enumeration may be used in the description of various embodiments. Unless otherwise expressly stated, the use of enumeration should not be construed as limiting the claims to any specific order or number of components. Nor should the use of enumeration be construed as excluding from the scope of the claims any additional steps or components that might be combined with or into the enumerated steps or components.

BRIEF DESCRIPTION OF THE DRAWINGS

FIG. 8 is a graph of an illustrative gross weight output from the load cell systems disclosed herein illustrating a manner of auto-zeroing a scale system; and FIG. 9 is another graph of an illustrative gross weight output from the load cell systems disclosed herein illustrating another manner of auto-zeroing a scale system when the scale system has already detected an object.

DETAILED DESCRIPTION OF THE EMBODIMENTS

Figure 1:
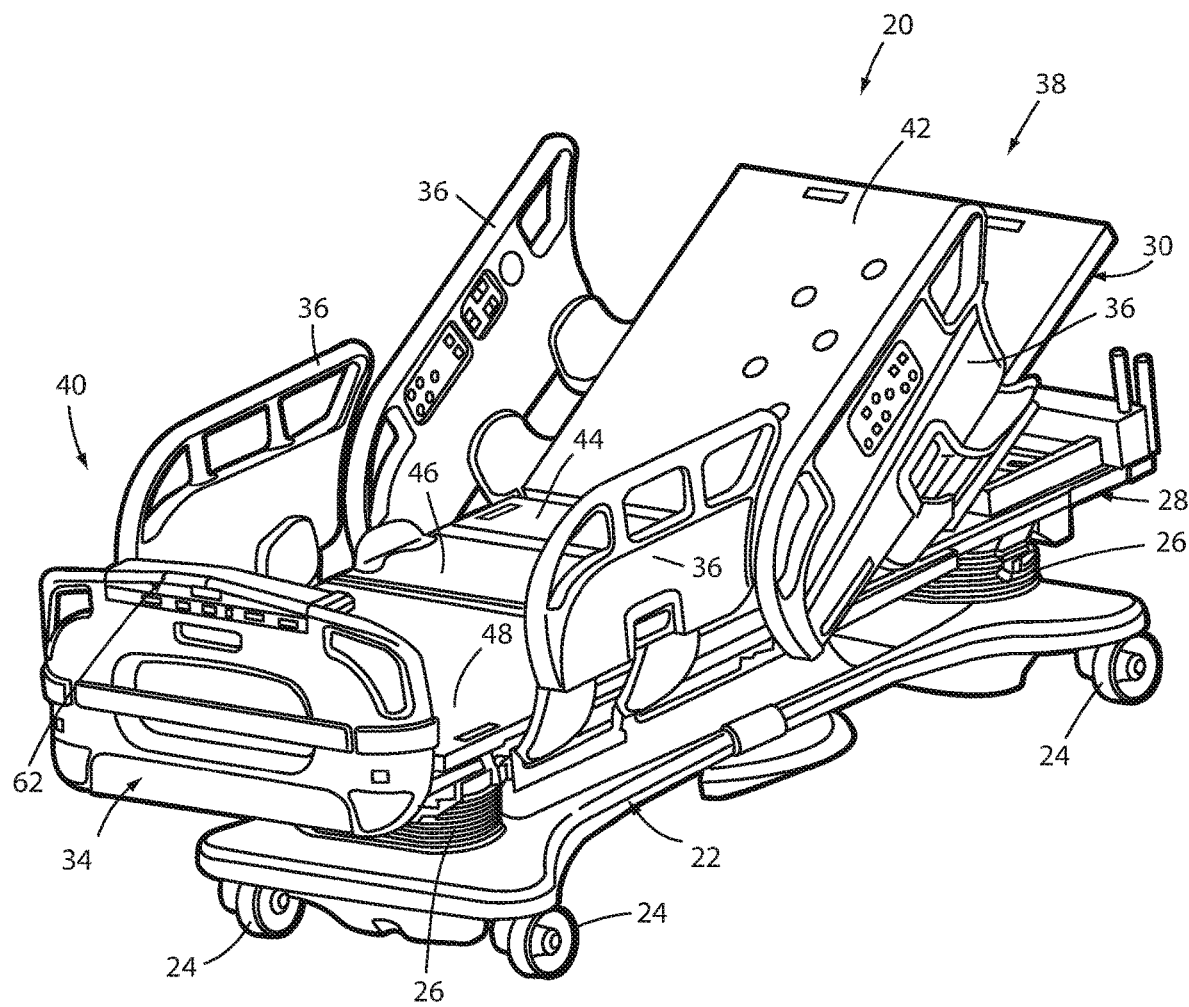
FIG. 1 is a perspective view of a person support apparatus according to a first embodiment.

An illustrative person support apparatus 20 according to a first embodiment is shown in FIG. 1. Although the particular form of person support apparatus 20 illustrated in FIG. 1 is a bed adapted for use in a hospital or other medical setting, it will be understood that person support apparatus 20 could, in different embodiments, be a cot, a stretcher, a gurney, a recliner, an operating table, a residential bed, or any other structure capable of supporting a person, whether stationary or mobile and/or whether medical or residential.

In general, person support apparatus 20 includes a base 22 having a plurality of wheels 24, a pair of lifts 26 supported on the base, a litter frame 28 supported on the lifts 26, and a support deck 30 supported on the litter frame 28. Person support apparatus 20 further includes a footboard 34 and a plurality of siderails 36. Siderails 36 are all shown in a raised position in FIG. 1 but are each individually movable to a lower position in which ingress into, and egress out of, person support apparatus 20 is not obstructed by the lowered siderails 36.

Lifts 26 are adapted to raise and lower litter frame 28 with respect to base 22. Lifts 26 may be hydraulic actuators, pneumatic actuators, electric actuators, or any other suitable device for raising and lowering litter frame 28 with respect to base 22. In the illustrated embodiment, lifts 26 are operable independently so that the tilting of litter frame 28 with respect to base 22 can also be adjusted. That is, litter frame 28 includes a head end 38 and a foot end 40, each of whose height can be independently adjusted by the nearest lift 26. Person support apparatus 20 is designed so that when an occupant lies thereon, his or her head will be positioned adjacent head end 38 and his or her feet will be positioned adjacent foot end 40.

Litter frame 28 provides a structure for supporting support deck 30, footboard 34, and siderails 36. Support deck 30 provides a support surface for a mattress (not shown in FIG. 1), or other soft cushion, so that a person may lie and/or sit thereon. The top surface of the mattress or other cushion forms a support surface for the occupant. Support deck 30 is made of a plurality of sections, some of which are pivotable about generally horizontal pivot axes. In the embodiment shown in FIG. 1, support deck 30 includes a head section 42, a seat section 44, a thigh section 46, and a foot section 48. Head section 42, which is also sometimes referred to as a Fowler section, is pivotable about a generally horizontal pivot axis between a generally horizontal orientation (not shown in FIG. 1) and a plurality of raised positions (one of which is shown in FIG. 1). Thigh section 46 and foot section 48 may also be pivotable about generally horizontal pivot axes.

Figure 2:
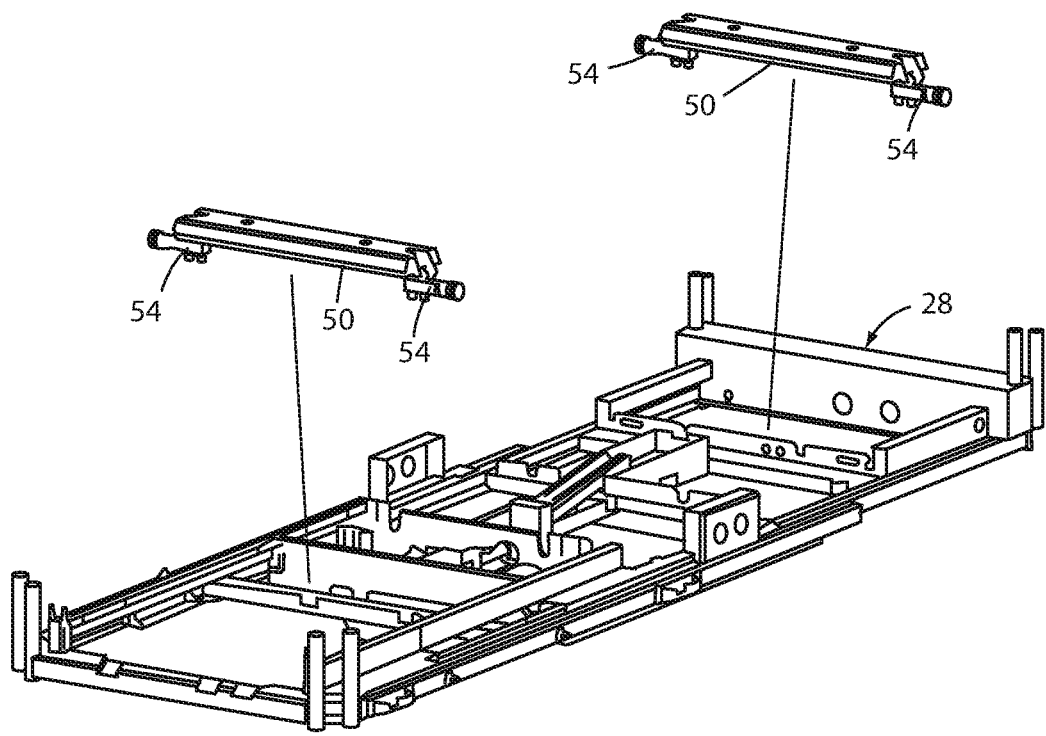
FIG. 2 is a perspective view of a litter and a pair of lift header assemblies with load cells of the person support apparatus of FIG. 1.

FIG. 2 illustrates in greater detail litter frame 28 separated from lifts 26 and base 22. Litter frame 28 is also shown in FIG. 2 with support deck 30 removed. Litter frame 28 is supported by two lift header assemblies 50. A first one of the lift header assemblies 50 is coupled to a top 32 (FIG. 3) of a first one of the lifts 26, and a second one of the lift header assemblies 50 is coupled to the top 32 of the second one of the lifts 26. Each lift header assembly 50 includes a pair of load cells 52. The illustrated embodiment of person support apparatus 20 therefore includes a total of four load cells 52, although it will be understood by those skilled in the art that different numbers of load cells may be used in accordance with the principles of the present disclosure. Load cells 52 are configured to support litter frame 28. More specifically, load cells 52 are configured such that they provide complete and exclusive mechanical support for litter frame 28 and all of the components that are supported on litter frame 28 (e.g. support deck 30, footboard 34, siderails 36, etc.). Because of this construction, load cells 52 are adapted to detect the weight of not only those components of person support apparatus 20 that are supported by litter frame 28 (including litter frame 28 itself), but also any objects or persons who are wholly or partially being supported by support deck 30.

Figure 3:
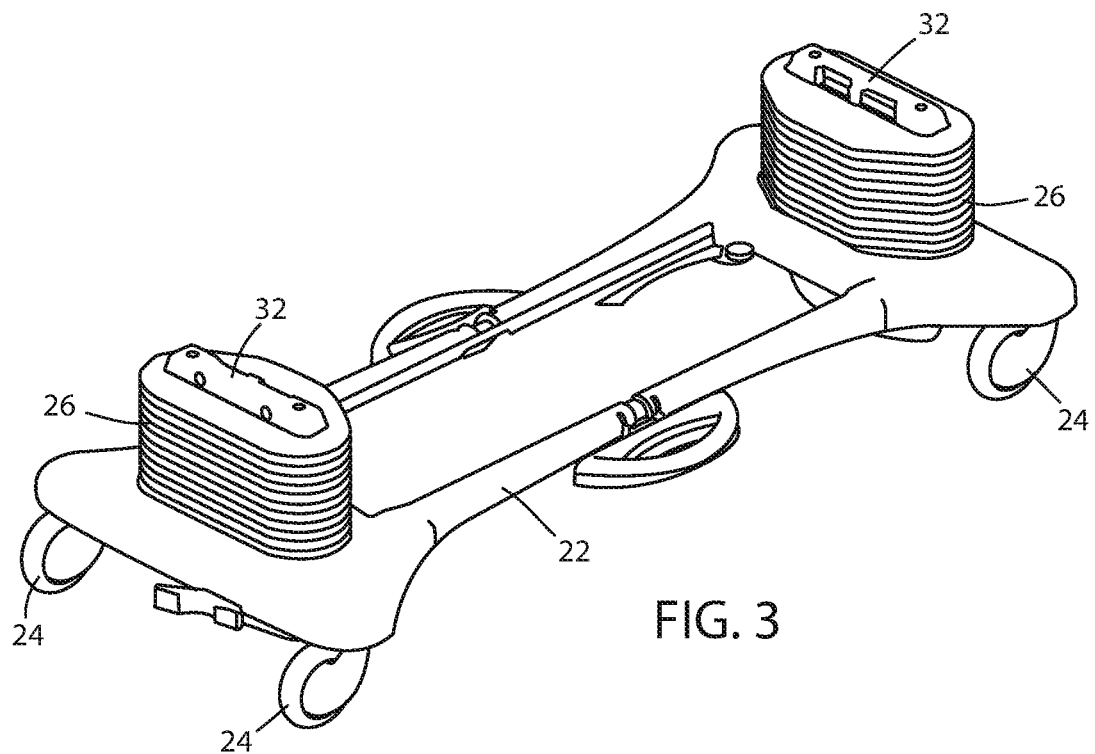
FIG. 3 is a perspective view of a base of the person support apparatus of FIG. 1.

The mechanical construction of person support apparatus 20, as shown in FIGS. 1-3, is the same as, or nearly the same as, the mechanical construction of the Model 3002 S3 bed manufactured and sold by Stryker Corporation of Kalamazoo, Mich. This mechanical construction is described in greater detail in the Stryker Maintenance Manual for the MedSurg Bed, Model 3002 S3, published in 2010 by Stryker Corporation of Kalamazoo, Mich., the complete disclosure of which is incorporated herein by reference. It will be understood by those skilled in the art that person support apparatus 20 can be designed with other types of mechanical constructions, such as, but not limited to, those described in commonly assigned, U.S. Pat. No. 7,690,059 issued to Lemire et al., and entitled HOSPITAL BED; and/or commonly assigned U.S. Pat. publication No. 2007/0163045 filed by Becker et al. and entitled PATIENT HANDLING DEVICE INCLUDING LOCAL STATUS INDICATION, ONE-TOUCH FOWLER ANGLE ADJUSTMENT, AND POWER-ON ALARM CONFIGURATION, the complete disclosures of both of which are also hereby incorporated herein by reference. The mechanical construction of person support apparatus 20 may also take on forms different from what is disclosed in the aforementioned references.

Figure 4:
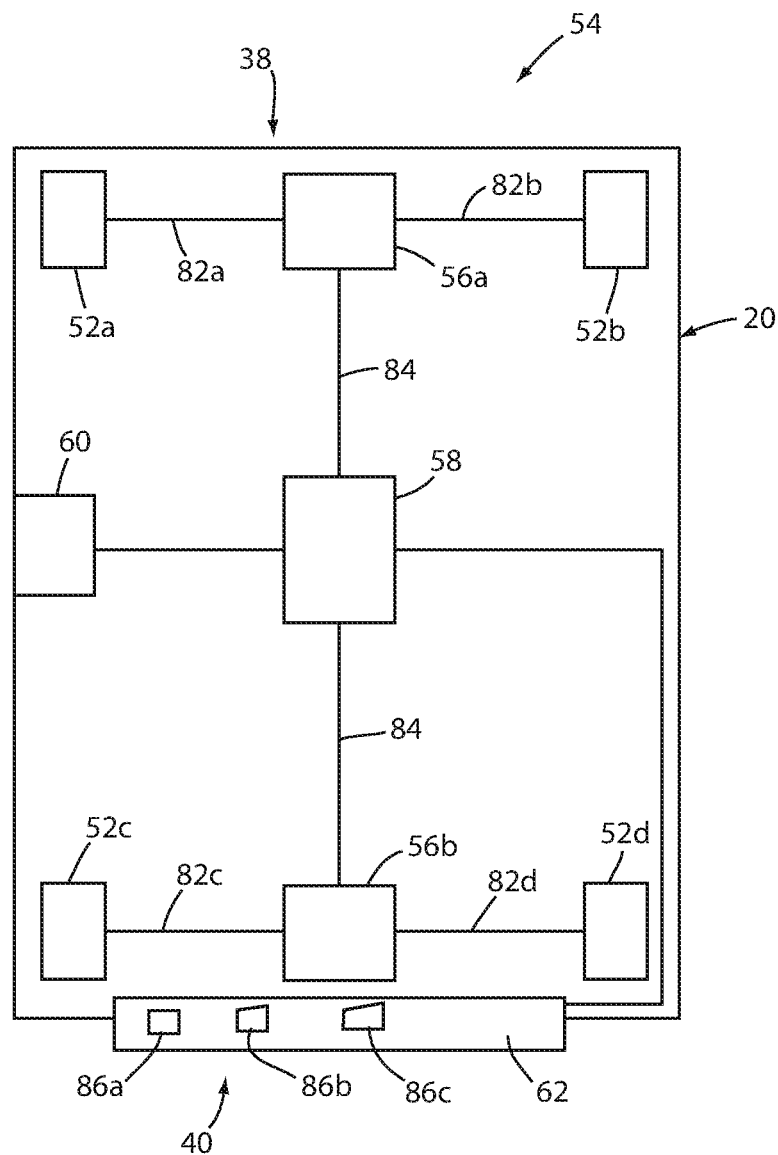
FIG. 4 is a plan view block diagram of a load cell system incorporated into a person support apparatus, such as the person support apparatus of FIG. 1.

Load cells 52 are part of a load cell system 54 (FIG. 4). Load cell system 54 includes, in addition to load cells 52, a first signal acquisition node 56a, a second signal acquisition node 56b, a controller 58, a communications module 60, and a control panel 62. Load cell system 54 functions as a scale system, an exit detection system, and/or an occupant monitoring system. When functioning as a scale system, load cell system 54 is adapted to measure the amount of weight that is supported on litter frame 28. Through the use of an automatic taring function described in more detail below, the weight of the litter frame 28 and other components of the person support apparatus 20 can be separated from the weight reading such that a weight of just the occupant of person support apparatus 20 can be determined.

When load cell system 54 functions as an exit detection system, load cell system 54 is adapted to determine when an occupant of person support apparatus 20 has left, or is likely to leave, person support apparatus 20, and to issue an alert and/or notification to appropriate personnel so that proper steps can be taken in response to the occupant's departure (or imminent departure) in a timely fashion. In at least one embodiment, load cell system 54 acts as an exit detection system by monitoring the distribution of mass or center of gravity of the patient using the system and method disclosed in commonly assigned U.S. Pat. No. 5,276,432 issued to Travis and entitled PATIENT EXIT DETECTION MECHANISM FOR HOSPITAL BED, the complete disclosure of which is incorporated herein by reference. Other manners for functioning as an exit detection system are also possible. Further, in some embodiments, load cell system 54 functions both as an exit detection system and as a scale system.

When operating as an occupant monitoring system, load cell system 54 is adapted to monitor movement of the occupant of person support apparatus 20, including keeping track of when the occupant enters and leaves person support apparatus 20, when objects are added to and/or removed from person support apparatus 20. In some embodiments, load cell system 54 may also or alternatively monitor one or more vital signs of the occupant, detect shivering of the occupant, and/or perform other occupant monitoring functions. When monitoring occupant movement, load cell system 54 may be configured to monitor such movement based on changes in the occupant's center of gravity or mass distribution, or on other factors. In at least one embodiment, load cell system 54 acts as an occupant monitoring system in any of the manners disclosed in commonly assigned U.S. patent application Ser. No. 14/873,734 filed Oct. 2, 2015, by inventors Marko Kostic et al. and entitled PERSON SUPPORT APPARATUS WITH MOTION MONITORING; and/or commonly assigned U.S. patent publication 2016/0022218 filed Mar. 13, 2014, by inventors Michael Hayes et al. and entitled PATIENT SUPPORT APPARATUS WITH PATIENT INFORMATION SENSORS, the complete disclosures of both of which are incorporated herein by reference. Load cell system 54 may also monitor movement of the occupant of person support apparatus 20 in other ways, including manners discussed in greater detail below.

Load cells 52 are positioned generally adjacent each corner of litter frame 28, as shown more clearly in FIG. 4. A head end set of load cells 52a, 52b is coupled to a head end signal acquisition node 56a by way of a pair of signal lines 82a and 82b. Signal lines 82a and 82b are wires, or other conventional communication media, that forward the analog outputs of load cells 52a, 52b to head end signal acquisition node 56a. A foot end set of load cells 52c, 52d is coupled to a foot end signal acquisition node 56b by way of a pair of signal lines 82c and 82d. Signal lines 82c and 82d, like signal lines 82a and 82b, are wires, or other conventional communication media, that forward the analog outputs of load cells 52c and 52d to foot end signal acquisition node 56b. Lines 82a-d are therefore analog signal lines that couple together two sets of load cells 52 to two signal acquisition nodes 56a and 56b.

Because lines 82a-d transmit analog signals, any electromagnetic interference or electrostatic discharges within the proximity of lines 82a-d are more likely to introduce errors into the analog signals transmitted to signal acquisition nodes 56a and 56b along lines 82a-d than if these lines were transmitting digital signals. In order to reduce such errors, signal acquisition node 56a is positioned generally midway between the head end set of load cells 52a and 52b, thereby ensuring that the physical lengths of lines 82a and 82b are as short as possible. These shortened lengths reduce the ability of the lines 82a, 82b to act as antennas for detecting electromagnetic interference and/or electrostatic discharges. Accordingly, head end signal acquisition node 56a is centered between load cells 52a and 52b in order to reduce the susceptibility of lines 82a and 82b to noise.

Foot end signal acquisition node 56b is similarly positioned at a location that is centered between foot end load cells 52c and 52d. As with head end signal acquisition node 56a, foot end signal acquisition node 56b's position midway between its neighboring load cells (52c and 52d) ensures that the physical length of lines 82c and 82d is as short as possible. This shortened length reduces the ability of the lines 82c, 82d to act as antennas for detecting electromagnetic interference and/or electrostatic discharges. Accordingly, foot end signal acquisition node 56b is centered between load cells 52c and 52d in order to reduce the susceptibility of lines 82c and 82d to noise.

Each signal acquisition node 56a and 56b communicates with controller 58 via a communication line 84. Communication lines 84, unlike signal lines 82, convey digital signals, rather than analog signals. Accordingly, communication lines 84 are far less susceptible to interference. As a result, the physical length of lines 84 is generally immaterial and controller 58 can be positioned at any suitable location on person support apparatus 20. Controller 58 therefore can be moved from the position generally in the center of person support apparatus 20, as shown in FIG. 4, to any suitable location on person support apparatus 20. Indeed, in some embodiments, controller 58 may be mounted on a common circuit board on which one of signal acquisition nodes 56 is also mounted. In other embodiments, each signal acquisition node 56 and controller 58 is mounted on its own circuit board.

Figure 5:
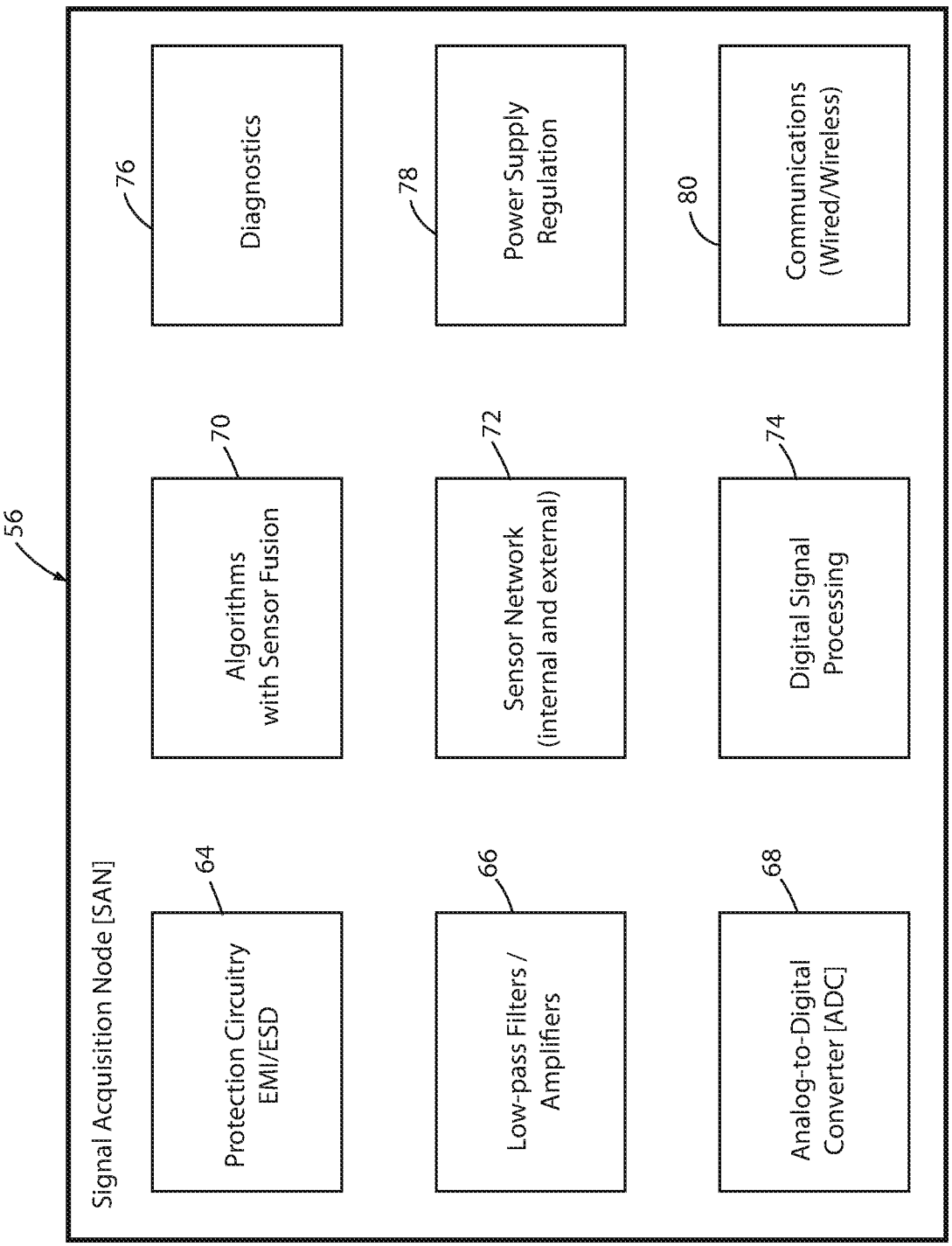
FIG. 5 is a detailed block diagram of a signal acquisition node of the load cell system of FIG. 4.

Although the composition of each signal acquisition node 56a, 56b may vary, FIG. 5 illustrates one illustrative embodiment of implementing signal acquisition node 56a and/or 54b. As shown therein, signal acquisition node 56 includes protection circuitry 64, one or more low pass filters and/or amplifiers 66, an analog-to-digital converter 68, memory 70 in which one or more algorithms are stored, a sensor network 72, a digital signal processor 74, a diagnostics module 76, a power supply 78, and communications circuitry 80.

Protection circuitry 64 (FIG. 5) includes one or more circuits adapted to reduce noise caused by electromagnetic interference (EMI) and/or electrostatic discharge (ESD) and to reduce or prevent its interference with the proper operation of load cells 52 and signal acquisition node 56. Low pass filter/amplifier 66 filters and/or amplifies the outputs from each load cell 52 that is fed into signal acquisition node 56 via signal lines 82 (FIG. 4). The cutoff frequency of the low pass filtering is chosen to remove high frequency components received from lines 82 that are due to noise and/or that represent signal components that are unrelated to the scale, exit alert, and/or occupant monitoring functions of load cell system 54.

In the illustrated embodiment, analog-to-digital (ND) converter 68 is at least a two channel A/D converter wherein a first channel converts the analog signals received from a first load cell (e.g. 52a) to digital signals and a second channel converts the analog signals from a second load cell (e.g. 52b) to digital signals (FIG. 4). The digital signals output from each channel of A/D converter 68 are then fed to digital signal processor 74 for further processing. In some embodiments, two separate single-channel A/D converters 68 are used in place of a single dual-channel A/D converter 68. Regardless of the number of channels and/or A/D converters 68, each A/D converter is capable of operating at different sampling rates. As will be discussed in greater detail below, the sampling rate at which the A/D converters 68 sample the analog signals received from lines 82 is varied by load cell system 54. The changes to this sampling rate are carried out, in at least one embodiment, by digital signal processor 74.

Memory 70 (FIG. 5) includes programming stored therein for carrying out one or more algorithms executed by digital signal processor 74. Such algorithms include algorithms for processing the outputs from load cells 52, as well as, in at least some embodiments, fusing the outputs from load cells 52 with the outputs from one or more additional sensors that feed into signal acquisition node 56. Such additional sensors may vary from embodiment to embodiment. In some embodiments, the additional sensors include one or more accelerometers adapted to detect accelerations caused by movement of the occupant of person support apparatus 20 while the occupant is positioned on support deck 30. One example of such an accelerometer sensing system is disclosed in commonly assigned U.S. patent application Ser. No. 62/253,167 filed Nov. 10, 2015, by inventors Marko Kostic et al. and entitled PERSON SUPPORT APPARATUSES WITH ACCELERATION DETECTION, the complete disclosure of which is incorporated herein by reference.

Another type of sensor whose data may be fused with the outputs from load cells 52 is a thermal image sensor adapted to capture thermal images of the occupant of person support apparatus 20 while the occupant is supported on person support apparatus 20. One example of a thermal imaging system with outputs suitable for fusing with the outputs of load cells 52 is disclosed in U.S. patent application Ser. No. 14/692,871 filed Apr. 22, 2015, by inventors Marko Kostic et al. and entitled PERSON SUPPORT APPARATUS WITH POSITION MONITORING, the complete disclosure of which is incorporated herein by reference. Another type of sensor whose data may be fused with the outputs from the load cells 52 is a sensor that detects the presence/absence of a component of person support apparatus 20 whose weight is detectable by load cell system 54. For example, a sensor may be used to detect if footboard 34 is present or not, or a headboard, or another component. Adjustments to the taring and/or zeroing functions of the load cell system can be made according to changes detected by these types of sensors. Still other types of sensors may be used whose outputs are fused with the outputs from load cells 52 and used for performing, or assisting in the performance of, one or more of the scale, exit detection, and/or occupant monitoring functions of load cell system 54.

Sensor network 72 (FIG. 5) refers to the load cells 52 that are coupled to signal acquisition node 56 by way of signal lines 82, as well as any other additional sensors that have their outputs fused together with the outputs of load cells 52.

Digital signal processor 74 (FIG. 5) is, in at least one embodiment, a conventional microcontroller. It will be understood, however, that digital signal processor 74 may take on other forms. In general, digital signal processor 74 may include any one or more microprocessors, microcontrollers, field programmable gate arrays, systems on a chip, volatile or nonvolatile memory, discrete circuitry, and/or other hardware, software, or firmware that is capable of carrying out the functions described herein, as would be known to one of ordinary skill in the art. Such components can be physically configured in any suitable manner, such as by mounting them to one or more circuit boards, or arranging them in other manners, whether combined into a single unit or distributed across multiple units. The instructions followed by digital signal processor 74 when carrying out the functions described herein, as well as the data necessary for carrying out these functions, are stored in memory 70.

Diagnostic circuits 76 (FIG. 5) include one or more circuits used by digital signal processor 74 for carrying out one or more diagnostic functions associated with signal acquisition node 56. In some embodiments, diagnostic circuits 76 include one or more of the circuits disclosed in commonly assigned U.S. patent application Ser. No. 15/185,623 filed Jun. 17, 2016, by inventors Marko Kostic et al. and entitled PERSON SUPPORT APPARATUS WITH LOAD CELLS, the complete disclosure of which is incorporated herein by reference. Other types of diagnostic circuits can, of course, be used.

Power supply 78 (FIG. 5) includes circuitry for regulating the electrical power supplied to signal acquisition node 56 and load cells 52. Such circuitry 78 may include conventional components and designs for regulating and supplying electrical power, including, but not limited to, circuitry for rectifying alternating current (AC) to direct current (DC) and/or circuitry for changing the supplied voltage levels to voltage levels suitable for the electrical components of load cell system 54.

Communications circuitry 80 (FIG. 5) provides communication abilities to signal acquisition node 56 enabling it to communicate with controller 58 over communication line 84 (FIG. 4). As noted previously, communication lines 84 are digital communication lines in the illustrated embodiment. This contrasts with signal lines 82, which are analog. Communication lines 84 are, in at least one embodiment, wired communication paths. Such wired communication may be implemented using any of the following: a Controller Area Network (CAN) bus, a Local Interconnect Network (LIN) bus, Firewire, I-squared-C, RS-232, RS-485, a Universal Serial Bus (USB), and/or a Serial Peripheral Interface (SPI) bus. Other types of communication protocols may also be used, including wireless communication.

Communications circuitry 80 includes transceivers and/or other circuitry necessary for implementing the particular communication protocol used by signal acquisition node 56. In some embodiments, communication lines 84 may be Ethernet lines, such as disclosed in commonly assigned U.S. patent application Ser. No. 14/622,221 filed Feb. 13, 2015, by inventors Krishna Bhimavarapu et al. and entitled COMMUNICATION METHODS FOR PATIENT HANDLING DEVICES, the complete disclosure of which is incorporated herein by reference. In such instances, communication circuitry 80 includes one or more Ethernet interfaces and/or magnetics for implementing Ethernet communications with controller 58.

Controller 58 communicates with each signal acquisition node 56a, 56b, as well as communications module 60 and control panel 62 (FIG. 4). Communications module 60 includes one or more transceivers that communicate with one or more off-board devices. In one embodiment, module 60 includes a WiFi radio adapted to communicate with wireless access points of a healthcare facility's computer network, thereby enabling the person support apparatus 20 to communicate wirelessly with the computer network of the healthcare facility. Module 60 may also or alternatively include an Ethernet connection, or other wired circuitry, for enabling wired communication with the hospital network, as well as nurse call cable circuitry for coupling to a nurse call cable that communicates with a nurse call system of a healthcare facility.

Controller 58, as with digital signal processors 74, is a microcontroller, in at least one embodiment. In other embodiments, controller 58 may include any one or more microprocessors, microcontrollers, field programmable gate arrays, systems on a chip, volatile or nonvolatile memory, discrete circuitry, and/or other hardware, software, or firmware that is capable of carrying out the functions described herein, as would be known to one of ordinary skill in the art. Such components can be physically configured in any suitable manner, such as by mounting them to one or more circuit boards, or arranging them in other manners, whether combined into a single unit or distributed across multiple units. The instructions followed by controller 58 in carrying out the functions described herein, as well as the data necessary for carrying out these functions, are stored in a memory (not labeled) accessible to controller 58.

The analog outputs from load cells 52 are passed via lines 82 to signal acquisition nodes 56a and 56b (FIG. 4). After having high frequency components removed via low pass filters/amplifiers 66, each signal acquisition node 56 converts the analog signals received via line 82 into digital signals using analog-to-digital converters 68. In addition to converting the analog load cell signals into digital signals, each signal acquisition node 56 also scales the outputs from the individual load cells 52 and/or calibrates the outputs from each load cell 52. This scaling and/or calibration is performed by signal processor 74 of each signal acquisition node 56 and is based, at least partly, upon individual characteristics of each load cell 52. After the digitized outputs from each load cell have been processed by signal processor 74, they are transmitted via communications circuitry 80 over communication lines 84 to controller 58. As mentioned previously, in some embodiments, one or more additional sensors feed their outputs into signal acquisition nodes 56. In those embodiments, the outputs from the additional sensors are digitized, scaled, calibrated, and/or otherwise processed by signal processor 74 before being transmitted over lines 84 to controller 58.

The data that is transmitted over line 84 to controller 58 is time stamped, or otherwise indexed, so that controller 58 is able to match the data received from head end signal acquisition node 56a with the data received from foot end signal acquisition node 56b. In other words, the messages transmitted over lines 84 to controller 58 include a time stamp or other type of indexing feature to allow controller 58 to match the readings from load cells 52a and 52b that were taken at time X with the readings from load cells 52c and 52d that were also taken at time X (or, in some cases, the readings from load cells 52*c* and 52*d* that were taken at a time that most closely matches time X). If data from other sensors is also forwarded to controller 58, such time stamping or indexing features may also be sent with that data as well.

Controller 58 processes the data from signal acquisition nodes 56 in different manners depending upon how load cell system 54 is being used at a given time. As noted previously, load cell system 54 may be used as a scale, as an exit detection system, and/or as an occupant monitoring system. Control panel 62 includes a scale control 86*a* (FIG. 4) that is selectable by a user of person support apparatus 20. When the scale control 86*a* is selected, controller 58 processes the load cell data from signal acquisition nodes in a manner that yields an accurate weight of the occupant. This is accomplished by summing the measurements from all of the load cells 52 that were taken at the same time, or substantially the same time. Multiple measurements may be used in some embodiments that are then averaged or otherwise combined.

Control panel 62 also includes an exit detection control 86*b* (FIG. 4) that, when selected, arms an exit detection system. When the exit detection system is armed, controller 58 processes the data from signal acquisition nodes 56 to determine if the occupant is moving in a manner suggestive of an impending exit from person support apparatus 20, and/or to determine if the occupant has exited from person support apparatus 20. If either condition is present, controller 58 issues an alert, which may be both local to person support apparatus 20 and/or remote to person support apparatus 20 (the remote alert is accomplished by sending an alert message to a remote device via communications module 60).

When the exit detection system is armed, controller 58 determines if the occupant is about to exit, or already has exited, from person support apparatus 20 by computing a center of gravity of the occupant of person support apparatus 20 using the digital data supplied by signal acquisition nodes 56, and then comparing the center of gravity to one or more zones or other boundary criteria. Alternatively, controller 58 determines if the occupant is about to exit, or already has exited, from person support apparatus 20 by determining a distribution of the weights detected by each load cell 52 and comparing the detected weight distribution to one or more thresholds. The weight distribution uniquely identifies the center of gravity whether the center of gravity is explicitly calculated or not.

In some embodiments, person support apparatus 20 does not include an occupant monitoring control. Instead, controller 58 is adapted to automatically monitor the movement of the occupant whenever person support apparatus 20 is powered, or automatically monitor the movement of the occupant based on one or more other conditions. In other embodiments, control panel 62 may include an occupant monitoring control (e.g. control 86*c* of FIG. 4) that allows a user to selectively start and stop the occupant monitoring function. The occupant monitoring function includes monitoring whether the occupant is present or absent on person support apparatus 20, keeping track of the times when the occupant exits from, and returns to, person support apparatus 20, and, in some embodiments, tracking the movement of the occupant when he or she is present on person support apparatus 20.

Further, in some embodiments, as will be discussed in greater detail below, the occupant monitoring function also includes an automatic taring function that automatically calculates a tare weight reading. The tare weight reading is stored in memory and used to automatically compute the weight of the occupant after he or she enters or leaves person support apparatus 20. Tare weight readings may also be determined automatically at other times in order to detect and determine the changes in weight associated with the addition and removal of objects from person support apparatus 20. The tare weight readings are used in some embodiments to distinguish the weight of the occupant of person support apparatus 20 from the weight of non-patient items, such as the physical components of support deck 30, litter frame 28, bedding, pillows, etc. By knowing the tare weight, controller 58 is able to automatically zero the scale system by subtracting the tare weight from the current weight reading. If the occupant is absent from person support apparatus 20, the result of this subtraction is zero. If the occupant is present, the result of this subtraction is the patient's weight.

Still further, in some embodiments, the occupant monitoring function includes monitoring one or more of the occupant's vital signs when supported on person support apparatus 20. Alternatively, control panel 62 may include a separate vital signs monitoring control that, when activated, instructs load cell system to start or stop monitoring one or more vital signs of the occupant. In some embodiments, the vital signs include the occupant's breathing rate and heart rate. The monitoring of the occupant's heart rate is made possible by the forces transferred onto support deck 30 from the occupant's heartbeat, which are detectable by load cells 52. Similarly, the monitoring of the occupant's breathing is made possible by the forces transferred onto support deck 30 from the expansion and contraction of the occupant's chest cavity as he or she breathes, and these forces are also detectable by load cells 52. Illustrative manners of detecting a person's heart rate and breathing rate that may be used with any of the load cell systems disclosed herein are disclosed in commonly assigned U.S. Pat. No. 7,699,784 issued Apr. 20, 2010, to David Wan Fong et al. and entitled SYSTEM FOR DETECTING AND MONITORING VITAL SIGNS, the complete disclosure of which is incorporated herein by reference. The detection of the occupant's vital signs using load cells 52 may be augmented, or supplanted, with any of the methods disclosed in commonly assigned U.S. patent application Ser. No. 62/253,167, which has previously been incorporated herein by reference.

In the embodiment illustrated in FIG. 4, when a user selects the scale control 86*a*, controller 58 sends a message along lines 84 to each of the signal acquisition nodes 56 informing them that the user has selected the scale function. In response to this message, each digital signal processor 74 sends a control signal to its associated A/D converter 68 causing the A/D converter to switch from a higher sampling rate to a lower sampling rate. To the extent the A/D converter 68 was already operating at a lower sampling rate (as will be discussed more below), A/D converter 68 continues to operate at the lower sampling rate until a control signal is subsequently received from digital signal processor 74 causing it to change sampling rates.

The values of the higher and lower sampling rates may vary, depending upon the design of the specific A/D converter 68 used, the circuitry of load cell system 54, the desired range of frequencies to be detected by load cells 52, and/or other factors. In one embodiment, the lower sampling rate refers to a sampling rate of 1 to 100 Hertz, and the higher sampling rate refers to a sampling rate of approximately 1000 Hertz or more. Other sampling rate ranges, however, can be used for the higher and lower sampling rates. In some embodiments, any ranges may be used where the higher sampling rate is ten or more times as fast as the lower sampling rate. Still further, in some embodiments, controller 58 is configured to select between more than two sampling rates, thereby instructing the A/D converters 68 to operate at at least three different sampling rates, depending upon the particular function being carried out by load cell system 54 at that time.

The different sampling rates used by A/D converters 68 result in different levels of accuracy of the digitized outputs from the A/D converters 68, as would be known to a person of ordinary skill in the art. When an A/D converter is operating at a higher sampling rate, the accuracy of the digitized outputs are lower than when the A/D converter is operating at a lower sampling rate. Operating at a lower sampling rate, however, reduces the ability of the A/D converter to detect oscillations in the load cell outputs. As is known from the Nyquist-Shannon sampling theorem, the A/D converters 68 cannot accurately reproduce signals from the load cells that oscillate at frequencies greater than half the frequency of their sampling rates. Accordingly, controller 58 generally switches the sampling rates of A/D converters 68 between the two sampling rates depending upon the changing functions of load cell system 54, i.e. whether load cell system 54 is being used in a manner where accuracy of weight is desired or whether load cell system 54 is being used in a manner where it is desirable to detect load cell oscillations having frequencies of more than half the sampling rate that aren't otherwise detectable without aliasing.

As noted previously, when a user selects the scale function using the scale control 86a, controller 58 sends a message to the signal acquisition nodes 56 instructing them to switch their A/D converters 68 to a lower sampling rate. This lower sampling rate continues for as long as it takes to obtain a successful weight reading. In some embodiments, the outputs from each of the load cells 52 is summed together multiple times while the A/D converters 68 are operating at the low sampling rate and the multiple sums are averaged. Controller 58 reports this average to control panel 62, in at least some embodiments.

In some embodiments, after the weight reading has been taken, signal acquisition nodes 56 automatically switch their respective A/D converters 68 back to their fast sampling rates. This automatic switching occurs when person support apparatus 20 is configured to automatically revert to the occupant monitoring function (in the absence of a user actively selecting the scale control 86a or the exit detection control 86b). If person support apparatus 20 is not configured to automatically revert to performing the occupant monitoring function when the scale function and/or exit detection functions are not active, controller 58 may continue to have A/D converters 68 process the load cell outputs at a slow sampling rate until a user takes an action, or an event occurs, that prompts controller 58 to instruct A/D converter 68 to switch to faster sampling rate.

When a user selects the exit detection control 86b on control panel 62 to activate the exit detection function (i.e. arm the exit detection system), controller 58 changes the sampling rate of A/D converters 68 in different manners, depending upon what other functions are being carried out by load cell system 54 at that time. For example, it is possible to simultaneously activate both the scale function and the exit detection function. If the scale function is activated at the same time the exit detection function is activated, controller 58 instructs A/D converters 68 to take samples at a slow rate. If the scale function is not activated and the exit detection function is activated, controller 58 instructs A/D converters 68 (via digital signal processors 74 of signal acquisition nodes 56) to take samples at the faster rate. If neither the scale control 86a nor the exit detection control 86b is activated, controller 58 instructs A/D converters 68 to take samples at the fast rate.

In at least one embodiment, controller 58 instructs the A/D converters 68 to take samples at the slower rate when scale control 86a is activated, and controls the sampling rates of the A/D converters 68 at other times based upon the outputs of the load cells. In such embodiments, some of which are discussed in greater detail below with respect to FIGS. 8 and 9, the sampling rate of the A/D converters 68 may vary automatically during time periods when the exit detection control 86b has been activated, and may also vary automatically during time periods when neither the exit detection control 86b nor the scale control 86a have been activated, such as when the occupant monitoring function is taking place. Still further, in some embodiments, such as, but not limited to, those embodiments where a patient's vital signs are being monitored, controller 58 may be configured to automatically switch to the faster sampling rate at all times when an accurate weight reading is not needed.

Figure 6:
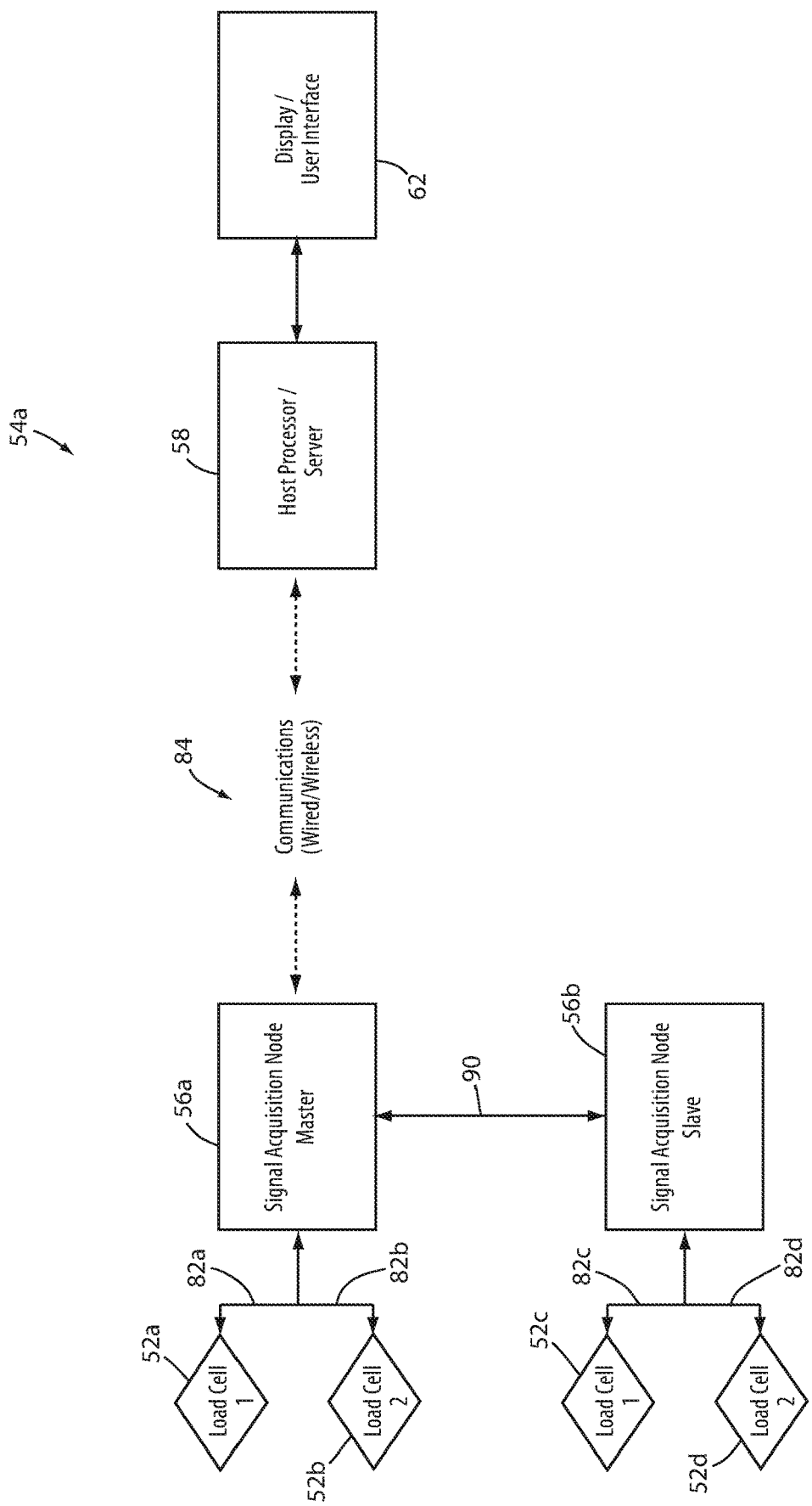
FIG. 6 is a block diagram of an alternative load cell system that may be incorporated into the person support apparatus of FIG. 1, as well as other person support apparatuses.

FIG. 6 depicts an alternative load cell system 54a that may be used with person support apparatus 20. Those components of load cell system 54a that are common to load cell system 54 are numbered with the same reference numbers. Those components of load cell system 54a that are not found in load cell system 54, or that are modified from load cell system 54, are provided with a new or modified reference number and described in more detail below. Load cell system 54a is adapted to implement and perform any or all of the functions described above with respect to load cell system 54. These include, but are not limited to, performing a scale function, acting as an exit detection system, monitoring movement of the occupant (including gross movement and/or shivering), and monitoring one or more vital signs of the occupant.

One of the differences between load cell system 54a and load cell system 54 is the addition of a communications channel 90 directly between head end signal acquisition node 56a and foot end signal acquisition node 56b. Channel 90 is a digital communications channel that may be implemented in any of the various manners described above with respect to communication lines 84 (e.g. a CAN bus, a LIN bus, Firewire, I-squared-C, RS-232, RS-485, USB, an SPI bus, Ethernet, etc.). Foot end signal acquisition node 56b sends the digitized, filtered, and (in some cases) processed outputs from load cells 52c and 52d to head end signal acquisition node 56a via communication channel 90, unlike signal acquisition node 56b of load cell system 54, which sends this information directly to controller 58. Digital signal processor 74 of head end signal acquisition node 56a uses the signals from foot end signal acquisition node 56b to compute the detected weight, movement, and/or vital signs of the occupant of person support apparatus 20. The computed outputs are then forwarded to controller 58 which takes one or more steps in response (e.g. displaying information from load cell system 54a on a display of control panel 62, forwarding information from load cell system 54a to another device via communications module 60, etc.).

Head end signal acquisition node 56a computes a detected weight, movement (including, but not limited to, movement indicative of an exit from person support apparatus 20), and/or vital signs of the occupant in any of the manners previously described with respect to controller 58 and load cell system 54. In performing these calculations, head end signal acquisition node 56a changes the sampling rate of its A/D converter 68 and sends commands via channel 90 to the A/D converter 68 of foot end signal acquisition node 56*b* to change its sampling rate. The changes to the sampling rates are carried out in accordance with any of the algorithms described above with respect to load cell system 54 (e.g. switching to a slow rate when weighing the occupant, switching to a faster rate when detecting vital signs, shivering, and/or movement, etc.).

Load cell system 54*a* thus differs from load cell system 54 primarily in that the computational burden of processing the outputs from the two signal acquisition nodes 56*a* and 56*b* is offloaded from controller 58 to the digital signal processor 74 of head end signal acquisition node 56*a*. It will, of course, be understood by those skilled in the art that load cell system 54*a* may be modified so that the computational burden is offloaded to digital signal processor 74 of foot end signal acquisition node 56*b* instead. In this modified embodiment, head end signal acquisition node 56*a* sends the digitized outputs from load cells 52*a* and 52*b* over channel 90 to foot end signal acquisition node 56*b* for processing. Foot end signal acquisition node 56*b* thereafter shares the processed results with controller 58 via a communication line 84 that extends therebetween (not shown in FIG. 6).

Figure 7:
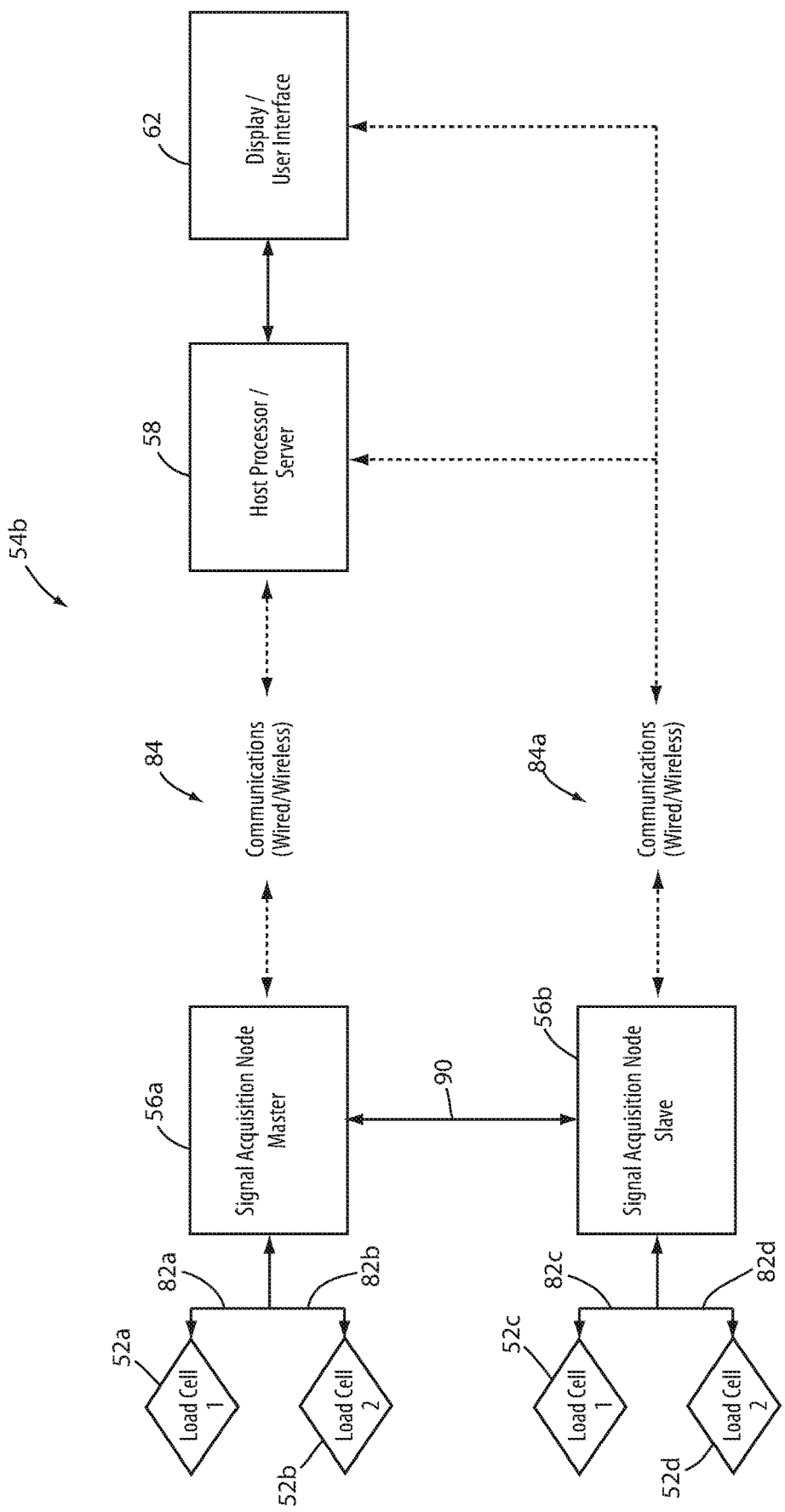
FIG. 7 is a block diagram of yet another alternative load cell system that may be incorporated into the person support apparatus of FIG. 1, as well as other person support apparatuses.

FIG. 7 depicts another alternative load cell system 54*b* that may be used with person support apparatus 20. Those components of load cell system 54*b* that are common to load cell systems 54 and/or 54*a* are numbered with the same reference numbers. Those components of load cell system 54*b* that are not found in load cell systems 54 or 54*a*, or that are modified from load cell systems 54 or 54*a*, are provided with a new or modified reference number and described in more detail below. Load cell system 54*b* is adapted to implement and perform any or all of the functions described above with respect to load cell systems 54 and 54*a*. These include, but are not limited to, performing a scale function, acting as an exit detection system, monitoring movement of the occupant, monitoring one or more vital signs of the occupant, and in some instances, detecting shivering by the occupant.

Load cell system 54*b* includes a communication channel 90 that communicatively couples head end and foot end signal acquisition nodes 56*a* and 56*b* together. Unlike load cell system 54*a* where one of the nodes 56*a*, 56*b* sends its digitized outputs to the other node, both of the nodes 56*a* and 56*b* send their digitized data to each other. That is, each signal acquisition node 56*a* and 56*b* processes the outputs from its own two connected load cells 52 (received on signal lines 82) as well as the outputs from the other two load cells that are connected to the other signal acquisition node (received via communication channel 90). Signal acquisition nodes 56*a* and 56*b* therefore perform redundant processing. This is done in order to guard against failure of the entire load cell system 54*b* if either signal acquisition node 56 or 56*b* individually fails. This helps ensure that load cells system 54*b* continues to operate properly in the face of a single signal acquisition node failure.

In order to fully implement this redundancy, load cell system 54*b* further includes a second communication line 84*a* that extends between foot end signal acquisition node 56*b* and controller 58. The outputs from all four load cells 52*a-d* that are processed by signal acquisition node 56*a* are sent to controller 58 via communication line 84 while the outputs from all four load cells 52*a-d* that are processed by signal acquisition node 56*b* are sent to controller 58 via communication line 84*a*. Communication lines 84 and 84*a* therefore provide redundant communication pathways that allow the continued operation of load cell system 54*b* in the event of the failure of one of these. In at least one embodiment, controller 58 is programmed to select one of the sets of redundant outputs (from nodes 56*a* or 56*b*) for further processing, display, and/or forwarding. In the event one set of these redundant outputs fails, controller 58 switches to using the other set of redundant outputs.

FIG. 8 depicts a graph 92 of the gross weight sensed by load cells 52 over a time period in which an occupant enters person support apparatus 20. This graph illustrates one manner in which any of load cell systems 54, 54*a*, and/or 54*b* may implement an automatic-zeroing function that renders it unnecessary to manually zero the scale prior to the occupant entering person support apparatus 20. The automatic-zeroing function not only zeroes the scale reading with respect to the weight present on person support apparatus 20 prior to the occupant entering person support apparatus 20, but also automatically zeros the scale reading while the occupant is supported on person support apparatus 20 and objects are added to, or removed from, person support apparatus 20. Further, as will be discussed in greater detail below, this graph illustrates one manner in which transitions between the slow and fast sampling rates of A/D converters 68 may be carried out.

As shown in FIG. 8, during an initial time period 94, the gross weight 96 detected by the load cells 52*a-d* remains generally steady. While this gross weight is generally steady, controller 58 (or digital signal processors 74 of signal acquisition nodes 56*a*, 56*b*) instructs A/D converters 68 to periodically take readings at a low sampling rate. As shown in FIG. 8, the low sampling rate readings occur during short periods of time that are labeled A. These short periods of time may last for a few seconds, or for different lengths of time. During these short periods of time, one or more readings from the load cells 52 are taken using the low sampling rate of the A/D converters. These one or more readings are used to generate an accurate reading of the gross weight detected by the load cells 52 during these time periods A. This accurate weight reading is a tare weight reading and is indicated by the letter T in FIG. 8. This value is stored in a memory of person support apparatus 20 and used later when calculating a weight of an occupant, as discussed in greater detail below. In between the time periods labeled A in FIG. 8, readings from the A/D converters are taken at a fast sampling rate, as will be discussed more below.

It will be understood that the initial time period 94 shown in FIG. 8 is of an arbitrary length that may vary in actual practice. However long or short the actual length of initial time period 94, the tare value T is determined from outputs of the load cells 52 using digitized samples gathered during one or more of the slow sampling rate time periods labeled A (which yield more accurate results). The initial time period transitions into an intermediate time period 98 when a change in the gross weight 96 is detected that is greater than a predefined threshold. If this change occurs during a time period A, it prompts load cell systems 54, 54*a*, and/or 54*b* to switch the sampling rates of the A/D converters to the fast sampling rate. If this change occurs between time periods A when a fast sampling rate is already in use, the fast sampling rate continues to be used. In either case, the fast sampling rate is used to take readings from the load cells 52 throughout the intermediate time period 98.

The intermediate time period 98 comes to an end when the amount of variation in the gross weight stabilizes (i.e. falls below a threshold for more than a threshold amount of time). Once intermediate time period 98 ends, load cell system 54, 54*a*, and/or 54*b* periodically switches its A/D converter sampling rates back to the slow rates for the brief amounts of time labeled A. In between time periods A of subsequent time period 100, the A/D converters are switched back to their high sampling rate. During at least one of the time periods A of the subsequent time period 100, the load cell system determines a gross weight value P. This represents the gross weight detected by the load cell system after the occupant has entered person support apparatus 20. The load cell system (54, 54a, or 54b) thereafter automatically determines the occupant's weight by subtracting the tare weight T from the gross weight value P. The particular component of the load cell system 54, 54a, or 54b that performs these calculations may vary in these systems between controller 58 and the digital signal processors 74 of the signal acquisition nodes 56a, 56b.

The load cell system concludes that the weight that was added to person support apparatus 20 during the intermediate time period 98 is that of an occupant if the difference between the tare weight T and the gross weight value P is greater than a threshold S. If this difference is less than the value of the threshold S, then the load cell system concludes that the added weight corresponds to an object having been added to person support apparatus 20, rather than an occupant. Because the load cell system automatically determines the tare weight T prior to the occupant entering person support apparatus 20, it is not necessary for the user to manually activate a taring or zeroing function prior to the occupant entering person support apparatus 20, as in some prior art person support apparatuses.

In some embodiments, the load cell system is configured to also utilize other data when distinguishing between animate and inanimate objects being added to person support apparatus 20. For example, in some embodiments, the load cell system looks for the presence of vital signs during subsequent time period 100 (and in some cases, during initial time period 96 as well). If vital signs are detected, the load cell system concludes that an occupant has entered person support apparatus 20, even if the aforementioned weight difference is less than S. Alternatively, if no vital signs are detected, the load cell system concludes that no occupant has entered person support apparatus 20, even if the aforementioned weight difference exceeds the value S.

In some embodiments, controller 58 and/or one or more signal acquisition nodes 56 of load cell systems 54, 54a, and/or 54b are configured to compare outputs from the load cells 52 both during initial time period 94 and subsequent time period 100. In such embodiments, if vital signs are detected during initial time period 94, the load cell system concludes that an inanimate object has been added during the intermediate period, even if the object has a weight greater than threshold S. If vital signs are not detected during initial time period 94, but are detected during subsequent time period 100, the load cell system concludes that an occupant has entered person support apparatus. If vital signs are not detected during either initial time period 94 or subsequent time period 100, the load cell system concludes that an inanimate object was added to person support apparatus 20, regardless of whether the object's weight exceeds threshold S or not. Other conclusions and/or algorithms for using the vital signs may be incorporated into any of the load cell systems 54, 54a, and/or 54b.

Still further, either in addition to, or in lieu of, using vital signs to distinguish between animate and inanimate objects positioned on person support apparatus 20, any of the load cell systems 54, 54a, and/or 54b may look at changes in the center of gravity or mass distribution that exceed a threshold. If movement that is greater than a threshold is detected on the person support apparatus 20 after weight has been added or removed, this is indicative of person support apparatus being occupied by a person. If the previous weight change was a reduction in weight, then the reduction was likely due to an inanimate object being removed. If the previous weight change was an addition in weight, then the addition in weight was likely due to the person entering person support apparatus 20 (if the added weight was large enough to signify a person and/or no movement was detected prior to that weight addition), or it was likely due to an inanimate object being added (if the added weight was not large enough to signify a person and/or movement was detected prior to the weight addition). In addition to movement, the load cell system may also or alternatively look at the location of the added or removed weight to distinguish animate from inanimate objects. Occupants will tend to have their weight more centered while inanimate objects will tend to be added peripherally. Methods for monitoring the movement and/or location of added and removed weights are disclosed in more detail in commonly assigned U.S. patent application Ser. No. 14/873,734 filed Oct. 2, 2015, by inventors Marko Kostic et al. and entitled PERSON SUPPORT APPARATUS WITH MOTION MONITORING, the complete disclosure of which has already been incorporated herein by reference.

FIG. 9 depicts a graph 92a of the gross weight 96 sensed by load cells 52 over a time period in which both an inanimate object has been placed on person support apparatus 20 and the occupant has entered person support apparatus 20. This graph illustrates one manner in which any of load cell systems 54, 54a, and/or 54b may implement an automatic-zeroing function as well an automatic accounting of objects placed on person support apparatus 20. Graph 92a also illustrates a manner for transitioning between the slow and fast sampling rates of A/D converters 68.

As shown in FIG. 9, the load cell system (54, 54a, and/or 54b) calculates a tare weight T during an initial time period 94. This tare weight is labeled T1 in FIG. 9. The tare weight T1 is calculated during one or more of the slow sampling rate periods of time that are labeled A. Between these time periods A, readings are taken at the fast sampling rate. When a change in the load cell outputs (gross weight 96) is detected that exceeds a threshold, intermediate time period 98 commences and—if a fast sampling rate is not already being used—the sampling rate is switched to the high sampling rate. The high sampling rate continues through the intermediate time period 100.

After the changes in the gross weight subside below a threshold amount, intermediate time period 100 comes to an end, and the sampling rate is periodically switched back to a slow rate for short time periods A during subsequent time period 100. During one or more of these short time periods A of subsequent time period 100, the load cell system determines the gross weight, which in FIG. 9 is labeled T2. After T2 is determined, the load cell system subtracts T1 from T2 and compares this difference to the threshold S. Because this difference is less than the threshold S, the load cell system concludes that the weight that was added to the person support apparatus 20 during the intermediate time period 98 corresponds to an inanimate object, not the occupant.

During subsequent time period 100, the load cell system continues to monitor the gross weight reading 96 to look for changes that exceed a threshold magnitude and/or time. When such a change is detected, second intermediate time period 98a commences, as shown in FIG. 9. During this time period 98a, to the extent readings are not already being taken at the fast sampling rate, the load cell system switches to the fast sampling rate and continues to take readings at the fast sampling rate until the load cell readings settle. When the changes subside (i.e. the settling occurs), second intermediate period 98a ends and second subsequent time period 100a begins. During second subsequent time period 100a, the sampling rate of the A/D converters 68 is periodically switched back to the slow rate for brief periods of time A during which one or more gross weight readings are taken. These gross weight readings are identified by the letter P in FIG. 9. The load cell system subtracts the previous tare weight T2 from P and compares the resulting difference to threshold S. Because this difference exceeds S in this case, the load cell system concludes that the weight added to person support apparatus 20 during second intermediate time period 98a corresponds to an occupant.

Although not illustrated in FIG. 9 (or FIG. 8), the load cell system processes the removal of objects from person support apparatus 20 and the exit of the occupant from person support apparatus 20 in the same manner. That is, the load cell system determines the difference between the gross weight readings 96 after an intermediate period (e.g. 98, 98a, 98b, etc.) and the gross weight readings 96 immediately prior to that intermediate time period. The difference is then compared to the threshold. If the removed weight is greater than S, the load cell system concludes that the occupant has departed. If the removed weight is less than S, the load cell system concludes that an inanimate object has been removed from the person support apparatus 20.

For both FIGS. 8 and 9, the load cell system continues to monitor the gross weight 96 readings after subsequent time period 100 in FIG. 8 and the second subsequent time period 100a in FIG. 9. The continued monitoring is carried out in the same manner as previously described. That is, any changes in the gross weight reading that exceed a threshold magnitude and/or threshold time cause the system to switch to the fast sampling rate (if not already operating at the fast sampling rate). After such transitions settle (e.g. intermediate time periods 98a, 98b, etc.) the load cell system switches back to intermittently taking readings during brief time periods A using the slow sampling rate, and returning to the high sampling rate between time periods A. One or more of the readings taken during a time period A are used to calculates a gross weight. The control system compares the gross weight to the immediately prior tare weight and determines if the weight added (or subtracted) during the transition corresponds to a person or an inanimate object.

The load cell system (54, 54a, and/or 54b) keeps a record of the time at which all inanimate objects are added to, or removed from, person support apparatus 20, as well as a record of the time at which the occupant enters and leaves person support apparatus 20. Further, in some embodiments, the load cell system also calculates a total amount of time that the occupant has been on person support apparatus 20 and/or a total amount of time the occupant has been off of person support apparatus 20. These values are displayed on a display of control panel 62. This information gives a caregiver associated with the occupant of person support apparatus 20 an easily understandable measure of the mobility of the occupant. The caregiver is thus informed of how active or inactive the occupant of person support apparatus 20 is, and can take follow up steps, as appropriate, to encourage more activity of the occupant, particularly in cases where the occupant is a patient whose recovery will likely be hastened by increased physical activity.

In some embodiments, the load cell system is adapted to display a ratio of the amount of total amount of time the occupant has spent in person support apparatus 20 versus the total amount of time the occupant has spent out of person support apparatus 20, or vice versa. The ratio may be displayed over any desired time period. For example, the ratio may be calculated based upon the occupant's presence and absence from person support apparatus 20 over the last 24 hours, the last 48 hours, since the occupant first starting using person support apparatus 20, or some other time period. Control panel 62 is configured, in some embodiments, to allow a user to select the time period over which the ratio is calculated.

Still further, in some embodiments, person support apparatus 20 is configured to detect whether the occupant is asleep or not when supported on person support apparatus 20. One suitable manner for making this determination is disclosed in commonly assigned U.S. patent application Ser. No. 14/776,842 filed Sep. 15, 2015, by inventors Michael Hayes et al. and entitled PERSON SUPPORT APPARATUS WITH PATIENT INFORMATION SENSORS, the complete disclosure of which is incorporated herein by reference. In these embodiments, the load cell system 54, 54a, and/or 54b may be configured to calculate the ratio of the occupant's absence from and presence on person support apparatus 20 (or vice versa) for only those time periods during which the occupant is awake. In other words, the load cell system may provide the user with a measurement of how much of the occupant's waking hours he or she has spent on person support apparatus 20 versus how much of the occupant's waking hours he or she has spent off of person support apparatus 20. Still other manners of displaying the record of the occupant's absence/presence on person support apparatus 20, as well as the record of objects added and removed from person support apparatus 20, may be implemented.

In some embodiments of load cell systems 54, 54a, and/or 54b, once a steady state value of the gross weight 96 has been achieved in the initial or subsequent time periods 94 or 100 (FIGS. 8 and 9) and a slow sampling rate has been used to take an accurate weight reading during a time period A, the load cell system may switch back to the fast sampling rate and remain there until one or more events occur. In other words, instead of having time periods A occur periodically, time periods A can be modified to be aperiodic. Such events may include threshold-exceeding changes that occur over time in the readings taken at the high sampling rate, user inputs, and/or other events. Regardless of the trigger for switching back to the low sampling rate, the low sampling rate periods of time A allow more accurate weight readings to be taken. Conversely, when using the faster sampling rate, the load cell system may be better able to detect frequencies in the gross weight readings that are not otherwise detectable by the slow sampling rate. Such frequencies may correspond to the occupant's breathing, heart beat, or shivering, or to vibrations from a medical device or equipment positioned on or near person support apparatus 20, and/or from other sources.

In some embodiments of load cell system 54, 54a, and/or 54b, controller 58 and/or one or both of signal acquisition nodes 56a, 56b are configured to filter frequencies detected in the outputs of load cells 52 that are above a cutoff frequency. In those embodiments where the occupant's vital signs are detected, the cutoff frequency is selected to be higher than the highest expected vital sign. As one example, a person's heart rate might not be expected to rise above 150-200 beats per minute, in which case a cutoff frequency might be selected at somewhere between 300-400 Hertz, or something slightly above this range. By filtering out such frequencies, the components of the load cell outputs that are due to higher frequency vibrations are removed. As noted previously, such vibrations may result from medical equipment and/or devices that are positioned on or near person support apparatus 20, or from other sources.

In any of the embodiments of load cell systems 54, 54a, and 54b, one or more additional hardware lines may be added between controller 58 and the signal acquisition nodes 56a, 56b, and/or between the two signal acquisition nodes 56a, 56b. Over such hardware lines, the signal acquisition nodes 56a, 56b, and/or controller 58 may transmit a square wave, or other type of periodic signal. If this signal is not detected by the receiving structure (e.g. one of nodes 56a, 56b, or controller 58), this provides an indication of a fault in the transmitting structure. A sounding device (e.g. a buzzer) is coupled to the hardware line by a switch, or other structure, that closes in the absence of the periodic signal from the hardware line, thereby activating the sounder. The activation of the sounder provides an indication to the user of a fault in the load cell system. This method of notifying the user of a fault is entirely hardware implemented, and therefore continues to provide a notification to the user even in the presence of a software or processor fault with any of controller 58 and/or nodes 56a, 56b. Such a hardware-designed sounding devices helps ensure users that, in the absence of the activation of the sounding device, the load cell system is continuing to operate properly, which is desirable when the load cell system is being used to implement one or more safety-important functions (e.g. detecting patient exit, vital signs, shivering, etc.).

When load cell system 54, 54a, and/or 54b is being used to detect shivering of the occupant of person support apparatus 20, controller 58 is configured in some embodiments to send a message to an external device when the presence of shivering is detected. In some of these embodiments, the external device is a thermal control unit of the type disclosed in commonly assigned U.S. patent application Ser. No. 62/425,813 filed Nov. 23, 2016, by inventors Gregory Taylor et al. and entitled THERMAL SYSTEM, the complete disclosure of which is incorporated herein by reference. In such embodiments, the thermal control unit uses the shivering message from controller 58 of person support apparatus 20 as a confirmation of the detection of shivering by the thermal control unit. That is, the thermal control unit includes its own shivering sensors, but does not provide a shivering alarm to a user unless the shivering is detected by multiple sensors, such as those of the load cell system of person support apparatus 20 and one or more of the shivering sensors coupled to the thermal control unit. Alternative manners of processing the shivering message from person support apparatus 20 may be implemented.

Control panel 62, in addition to controlling various aspects of load cell systems 54, 54a, and 54b, may also include controls for controlling other aspects of person support apparatus 20 (e.g. motion). The control of these other functions may be carried out by controller 58, or they may be carried out by one or more other controllers that that are in communication with motors or other components that are controllable by control panel 62.

Various additional alterations and changes beyond those already mentioned herein can be made to the above-described embodiments. This disclosure is presented for illustrative purposes and should not be interpreted as an exhaustive description of all embodiments or to limit the scope of the claims to the specific elements illustrated or described in connection with these embodiments. For example, and without limitation, any individual element(s) of the described embodiments may be replaced by alternative elements that provide substantially similar functionality or otherwise provide adequate operation. This includes, for example, presently known alternative elements, such as those that might be currently known to one skilled in the art, and alternative elements that may be developed in the future, such as those that one skilled in the art might, upon development, recognize as an alternative. Any reference to claim elements in the singular, for example, using the articles "a," "an," "the" or "said," is not to be construed as limiting the element to the singular.

What is claimed is:

1. A person support apparatus comprising:
a frame;
a plurality of load cells supported by the frame, each of the plurality of load cells adapted to output analog signals indicative of loads detected by the load cells;
a support surface adapted to support thereon an occupant of the person support apparatus, the support surface being supported by the load cells such that a weight of the occupant is detectable by the load cells when the occupant is positioned on the support surface;
an analog-to-digital converter adapted to convert analog signals from at least one of the load cells into digital signals at a first rate and at a second rate; and
a controller adapted to switch the analog-to-digital converter between the first rate and the second rate based upon the digital signals output from the analog-to-digital converter, wherein the first rate is faster than the second rate and the controller is adapted to switch to the first rate when a change above a threshold amount occurs in the digital signals from the at least one of the load cells.

2. The person support apparatus of claim 1 wherein the controller is adapted to switch to the second rate when changes above the threshold amount are not detected for a threshold time in the digital signals from the at least one of the load cells.

3. The person support apparatus of claim 1 wherein the controller determines the weight of the occupant when the analog-to-digital converter is operating at the second rate.

4. The person support apparatus of claim 3 wherein the controller automatically determines a tare weight before the occupant enters the support surface.

5. The person support apparatus of claim 1 wherein the controller uses the digital signals from the at least one of the load cells to determine when the occupant enters the person support apparatus and when the occupant exits the person support apparatus.

6. A person support apparatus comprising:
a frame;
a plurality of load cells supported by the frame, each of the load cells adapted to output analog signals indicative of loads detected by the load cells;
a support surface adapted to support thereon an occupant of the person support apparatus, the support surface being supported by the load cells such that a weight of the occupant is detectable by the load cells when the occupant is positioned on the support surface;
a first signal acquisition node comprising a first analog-to-digital converter adapted to convert analog signals from a first one of the load cells into digital signals;
a second signal acquisition node spaced away from the first signal acquisition node, the second signal acquisition node comprising a second analog-to-digital converter adapted to convert analog signals from a second one of the load cells into digital signals; and
a controller spaced from the first and second signal acquisition nodes, the controller communicatively coupled to the first and second signal acquisition nodes and adapted to determine a weight supported on the support surface based upon the digital signals from the first and second signal acquisition nodes;

wherein the first signal acquisition node is adapted to send the digital signals from the first analog-to-digital converter to the second signal acquisition node, and the second signal acquisition node is adapted to send the digital signals from both the first and second analog-to-digital converters to the controller.

7. The person support apparatus of claim 6 wherein the first signal acquisition node and the first one of the load cells are both positioned adjacent a head end of the person support apparatus, and the second signal acquisition node and the second one of the load cells are both positioned adjacent a foot end of the person support apparatus.

8. The person support apparatus of claim 6 wherein the controller is adapted to automatically determine a tare weight of the support surface based on the digital signals from the first and second signal acquisition nodes.

9. The person support apparatus of claim 8 wherein the controller automatically determines the tare weight before the occupant enters the support surface.

10. The person support apparatus of claim 6 wherein both the first and second analog-to-digital converters are adapted to operate at a first rate and at a second rate.

11. The person support apparatus of claim 10 wherein the controller is adapted to instruct the first and second analog-to-digital converters which of the first and second rates to operate at.

12. The person support apparatus of claim 6 wherein the controller uses the digital signals from the first and second signal acquisition nodes to determine when the occupant enters the person support apparatus and when the occupant exits the person support apparatus.

13. A person support apparatus comprising:
a frame;
a plurality of load cells supported by the frame, each of the load cells adapted to output analog signals indicative of loads detected by the load cells;
a support surface adapted to support thereon an occupant of the person support apparatus, the support surface being supported by the load cells such that a weight of the occupant is detectable by the load cells when the occupant is positioned on the support surface;
a first signal acquisition node comprising a first analog-to-digital converter adapted to convert analog signals from a first one of the load cells into digital signals;
a second signal acquisition node spaced away from the first signal acquisition node, the second signal acquisition node comprising a second analog-to-digital converter adapted to convert analog signals from a second one of the load cells into digital signals; and
a controller spaced from the first and second signal acquisition nodes, the controller communicatively coupled to the first and second signal acquisition nodes and adapted to determine a weight supported on the support surface based upon the digital signals from the first and second signal acquisition nodes; wherein both the first and second analog-to-digital converters are adapted to operate at a first rate and at a second rate; and wherein the first signal acquisition node includes first processing circuitry adapted to analyze the digital signals from the first analog-to-digital converter to determine whether to operate the first analog-to-digital converter at the first rate or the second rate; and the second signal acquisition node includes second processing circuitry adapted to analyze the digital signals from the second analog-to-digital converter to determine whether to operate the second analog-to-digital converter at the first rate or the second rate.

14. A person support apparatus comprising:
a frame;
a plurality of load cells supported by the frame, each of the plurality of load cells adapted to output analog signals indicative of loads detected by the load cells;
a support surface adapted to support thereon an occupant of the person support apparatus, the support surface being supported by the load cells such that weight supported on the support surface is detectable by the load cells;
an analog-to-digital converter adapted to convert analog signals from at least one of the load cells into digital signals at a first rate and at a second rate; and
a controller adapted to detect when weight is added and removed from the support surface and to switch between the first and second rates based on detecting added weight and removed weight.

15. The person support apparatus of claim 14 wherein the first rate is more than one hundred times as fast as the second rate.

16. The person support apparatus of claim 15 wherein the controller automatically determines a tare weight.

17. The person support apparatus of claim 16 wherein the controller automatically distinguishes between weight changes resulting from the occupant entering or exiting the person support apparatus and weight changes resulting from objects added to or removed from the person support apparatus.

18. The person support apparatus of claim 14 wherein the load cells are part of an exit detection system having an armed state in which the controller issues an alert when the occupant exits the person support apparatus and a disarmed state in which the controller does not issue an alert when the occupant exits the person support apparatus, and wherein the controller is adapted to detect when weight is added and removed from the support surface when the exit detection system is in both the armed state and the disarmed state.

19. The person support apparatus of claim 18 wherein the controller is further adapted to automatically change the exit detection system to the armed state after the occupant enters the person support apparatus.

* * * * *